(12) United States Patent
Fahy

(10) Patent No.: US 6,869,757 B2
(45) Date of Patent: Mar. 22, 2005

(54) ADVANTAGEOUS CARRIER SOLUTION FOR VITRIFIABLE CONCENTRATIONS OF CRYOPROTECTANTS, AND COMPATIBLE CRYOPROTECTANT MIXTURES

(75) Inventor: Gregory M. Fahy, Corona, CA (US)

(73) Assignee: 21st Century Medicine, Inc., Rancho Cucamonga, CA (US)

( * ) Notice: Subject to any disclaimer, the term of this patent is extended or adjusted under 35 U.S.C. 154(b) by 0 days.

(21) Appl. No.: 09/916,396

(22) Filed: Jul. 27, 2001

(65) Prior Publication Data

US 2002/0076687 A1 Jun. 20, 2002

Related U.S. Application Data

(60) Provisional application No. 60/221,691, filed on Jul. 31, 2000.

(51) Int. Cl.$^7$ .............................. A01N 1/00; A01N 1/02
(52) U.S. Cl. .......................... 435/1.1; 435/1.2; 435/1.3; 435/2
(58) Field of Search .......................... 435/1.1, 1.2, 1.3, 435/2

(56) References Cited

U.S. PATENT DOCUMENTS

| | | | |
|---|---|---|---|
| 5,800,978 A | * | 9/1998 | Goodrich, Jr. et al. .......... 435/2 |
| 5,879,875 A | * | 3/1999 | Wiggins et al. .............. 435/1.1 |
| 6,194,137 B1 | * | 2/2001 | Khirabadi et al. ........... 435/1.3 |
| 6,395,467 B1 | * | 5/2002 | Fahy et al. ................... 435/1.3 |
| 2002/0045156 A1 | * | 4/2002 | Toner et al. .................... 435/2 |

FOREIGN PATENT DOCUMENTS

JP    1-106826    *   4/1989

OTHER PUBLICATIONS

Klebe et al., "Identification of new cryoprotective agents for cultured mammalian cells", In Vitro 19 (3 part I):167–70.*

Merck Index, entry 56, 1989.*

Williams et al., "Vial Breakage by Frozen Mannitol Solutions: Correlation with Thermal Characteristics and Effect of Stereoisomerism, Addivitves and Vial Configuration", J. Parenteral Science & Technology 45 (2):94–100 (1991).*

Ren et al., "The Crystallization Kinetics and the Critical Cooling Rates for Vitrification of Cryoprotective Solutions", Cryogenics 30:536–40 (1990).*

Fahy, Gregory M. and Ali, Suja E., Cryopreservation of the Mammalian Kidney, Cryobiology, 35: 114–1131, 1997.

Kheirabadi. Bijan S. and Fahy, Gregory M., Permanent Life Support By Kidneys Perfused with a Vitrifiable (7.5 Molar) Cryoprotectant Solution, Transplantation, 70: 51–57, 2000.

Khirabadi, Bijan S. and Fahy, Gregory M., Cryopreservation of the Mammalian Kidney—Transplantation of Rabbit Kidneys Perfused with EC and RPS–2 at 2–4° C$^{1,}$ Cryobiology, 31:10–25, 1994.

Kirabadi, B. S., Fahy, G.M., Merei, J., and Rasch, C., Does Substitution of Mannitol for Glucose Improve Euro–Collins as a Vehicle for Cryoprotective Agents?, Cryobiology, 35: 357, 1997.

Arnaud, Francoise, Khirabadi, Bijan S., Fahy, Gregory M., Normothermic blood perfusion of isolated rabbit kidneys, Transpl Int, 15: 278–289, 2002.

Fahy, Gregory M. et al., Cellular Injury Associated with Organ Cryopreservation: Chemical Toxicity and Cooling Injury, Cell Biology of Trauma, CRC Press, Boca Raton, Chapter 20: 333–356, 1995.

Rall, W. F. and Fahy, G. M., Ice–free cryopreservation of mouse embryos at—196° C by vitrification, Nature, 313: 573–575, 1985.

* cited by examiner

Primary Examiner—Sandra E. Saucier
(74) Attorney, Agent, or Firm—Stephen E. Reiter; Foley & Lardner LLP

(57) ABSTRACT

Disclosed herein is a carrier solution for cryoprotectants that is useful for use with cells, tissues, and whole organs and for a variety of cryoprotectant solutions and that permits antinucleators to be fully effective in vitrification solutions, thereby allowing vitrification solutions to attain extreme effectiveness, and compatible vitrification solution compositions for use with this carrier solution. The carrier solution comprises lactose and mannitol as well as other beneficial ingredients.

12 Claims, 3 Drawing Sheets

ADVANTAGEOUS CARRIER SOLUTION FOR VITRIFIABLE CONCENTRATIONS OF CRYOPROTECTANTS, AND COMPATIBLE CRYOPROTECTANT MIXTURES

RELATED APPLICATIONS

This application claims priority under 35 U.S.C. §119 of U.S. Provisional Application No. 60/221,691, filed Jul. 31, 2000.

FIELD OF THE INVENTION

The invention relates generally to the field of cryopreservation. More specifically, the present invention relates to extremely stable vitrification solutions of low toxicity and carrier solutions comprising lactose and mannitol.

BACKGROUND OF THE INVENTION

For vitrification solutions to be biologically applicable, the cryoprotectants that comprise the vitrification solution must be contained within a "carrier" or "vehicle" solution used to provide osmotic and physiological support for living systems in the presence and absence of the cryoprotectants. However, it is well known in the art that the efficacy of carrier solutions for cryoprotectants is unpredictable and that the best carrier solution for one cryoprotectant or cryoprotectant mixture may be different from the best carrier solution for another cryoprotectant or cryoprotectant mixture.

As disclosed in Fahy, et al., U.S. patent application Ser. No. 09/400,793, filed Sep. 21, 1999, glucose inhibits the action of the polyvinyl alcohol type "ice blocking" (antinucleating) agent. This renders Euro-Collins solution (containing 190 mM glucose) or RPS-2 (containing 180 mM glucose) sub-optimal for use with such antinucleating agents. However, the inclusion of such agents, typified most fully by a product called "X1000," which is commercially available from 21$^{st}$ Century Medicine, Rancho Cucamonga, Calif. 91730, is highly desirable. Several alternative carrier solutions were disclosed in Fahy, et al. U.S. patent application Ser. No. 09/400,793, filed Sep. 21, 1999, issued as U.S. Pat. No. 6,395,467 B1 (herein incorporated by reference), such as MHP-2, GHP-2, and RPS-T. However, none of these was fully satisfactory. These other carriers provided poorer recovery of tissues maintained in them in the presence of vitrifiable concentrations of cryoprotectant than does RPS-2, or are both prohibitively expensive (RPS-T) and may be less biologically acceptable than RPS-2.

The difficulties of not having an excellent carrier solution are multiplied when the object is to vitrify massive structures such as natural organs or tissue engineered products such as artificial organs or tissues. The only relevant experience known in the art has been the use of either RPS-2 (Fahy and Ali, *Cryobiology*, 35:114–131, 1997) or Euro-Collins solution (Khirabadi and Fahy, *Transplantation* 70:51–57, 2000; Khirabadi and Fahy, *Cryobiology* 31:10–25, 1994; Arnaud, Fahy, and Khirabadi, *Cryobiology* 35: 358, 1997, and paper submitted for publication 2001) for the perfusion of rabbit kidneys with a vitrification solution called VS4 (formula defined in those citations). Without the ability to use either Euro-Collins or RPS-2 as a carrier solution, the practitioner is unable to rely on the state of the art in selecting a carrier solution for use, particularly given the extreme desirability of using a vitrification solution other than VS4 or its more concentrated relative, VS41A (formula published in, for example, G. M. Fahy et al., Chapter 20, in "*Cell Biology of Trauma*" (J. J. Lemasters and C. Oliver, Eds.), CRC Press, Boca Raton, Fla., 1995, pp. 333–356). This lack of a suitable carrier solution is a major impediment to applying vitrification to whole organs and engineered systems. This is particularly true when one considers the potential differential response of the organ parenchyma and the organ vasculature to a particular untested combination of cryoprotectants and carrier solution.

SUMMARY OF THE INVENTION

It is one object of the present invention to describe an appropriate carrier solution for use with newer vitrification solutions, and to show vitrification solutions that are surprisingly effective in the presence of this new carrier solution. It is a further object to provide a carrier solution that gives excellent results when used both with isolated tissue slices and with whole organs and for a variety of newer-generation vitrification solutions.

DETAILED DESCRIPTION OF THE PREFERRED EMBODIMENT

Figure 1:
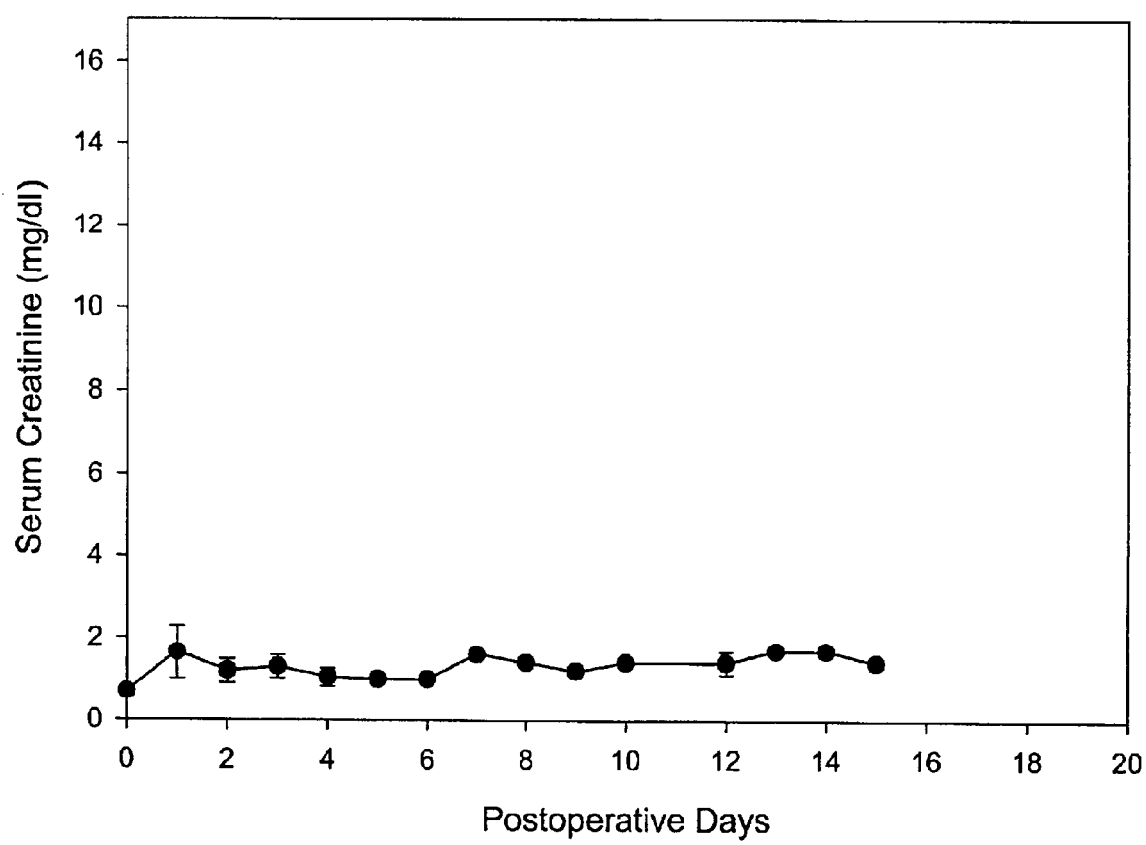
FIG. 1 shows the results of perfusing kidneys with a solution containing a combination of mannitol and lactose (LM5).

It is one object of the present invention to describe surprisingly effective vitrification solutions. These solutions were all derived by practicing the invention described in U.S. application Ser. No. 09/400,793, now U.S. Patent No. 6,395,467, filed Sep. 21, 1999, "Improved Cryoprotectant Solutions," by G. Fahy and B. Wowk (herein incorporated by reference) or by following these teaching plus the teachings in U.S. Pat. application No. 20020042042, "Hypertonic Reduction of Cooling Injury," by G.M. Fahy, filed Jul. 26, 2001 (herein incorporated by reference). However, the solutions described herein were so extraordinarily effective that their effectiveness was not predictable based on the teachings of these cited patent applications alone. Indeed, these solutions could not have been derived, and their value could not have been appreciated, without the development of another tool which was considered to be impossible at the time it was invented. This tool is the viability-stability diagram.

It is a further object of the present invention to describe new vitrification solution variations that are extraordinarily effective due to their somewhat surprising combined lack of toxicity and stability against ice formation as a result of seemingly minor variations in solution composition.

The viability-stability diagram is a plot of a viability measurement made after exposure to a cryoprotectant solution against the warming rate required to limit devitrification of that cryoprotectant solution to a tolerable level. The viability-stability diagram combines a biological measurement with a physical measurement to form a universal scale for ranking the effectiveness of a vitrification solution for a particular system. Typically, the effect of the solution on viability must be made after contact of the living system with the vitrification solution for a period long enough to render the living system vitrifiable upon subsequent cooling. Further, the level of devitrification selected for measurement must be realistically innocuous to the system under study in order for the diagram to have significance for predicting the outcome of a vitrification and rewarming experiment.

The warming rate required to suppress devitrification is determined by cooling the vitrification solution at a standard, realistic rate, and then rewarming the vitrified solution at a series of warming rates. The heat evolved during devitrification (devitrification is ice formation during warming) is quantitated using a differential scanning calorimeter and is plotted against the warming rate. By curve fitting such a heat evolution vs. warming rate plot through several points for a given solution, the intersection of the curve with a standard level of heat evolution can be determined, and the warming rate producing that degree of heat evolution can be read from the graph. This warming rate is the critical warming rate that is plotted against the measurement of viability to form a point on the viability-stability plot.

The concept of a viability-stability plot was introduced in "Improved Cryoprotectant Solutions", U.S. patent application Ser. No. 09/400,793, filed Sep. 21, 1999, issued as U.S. Pat. No. 6,395,467 B1 (herein incorporated by reference), but the plot provided was only an estimate based on visual observations of macroscopic samples. When more precise stability data were determined for many of the solutions listed in the parent application, much more revealing information became available. This new information permitted solution "fine-tuning" to combine those features that were associated with higher viability with those features that were associated with higher stability. As a result, extraordinarily effective solutions were derived, and these are provided herein.

In addition, recent insights into the role of impermeant tonicity on the magnitude of "cooling injury" in vitrifying systems, as disclosed in "Hypertonic Reduction of Chilling Injury", U.S. Pat. application Ser. No. 09/916,032, published as U.S. 2002/0042042, filed Jul. 26, 2001 (herein incorporated by reference), led to the solutions presented herein that combine low toxicity and high stability with extraordinarily strong protection against chilling injury. The resulting solutions are of unprecedented utility for the cryopreservation of living systems.

Solutions are reported herein that minimize toxicity, cooling injury, and devitrification. These solutions, used at full strength, are of particular importance for the cryopreservation of larger living systems, such as organs and engineered tissues and bioartificial organs, for which rapid cooling and warming is difficult or impossible. However, many living systems and some engineered tissues and bioartificial organs are capable of being cooled and warmed at higher rates than those discussed herein, or are capable of survival after more severe ice formation than is discussed herein. For these systems, appropriate dilutions of the tabulated formulas may also be effectively used, and may be more advantageous than the full strength versions. The use of dilutions of established vitrification solutions is taught, for example, in Rall, W. F., and Fahy, G. M., *Nature*, 313:573–575, 1985. Consequently, moderate dilutions of the presently disclosed formulae are considered to be equivalent to and to fall within the scope of the disclosed invention.

One embodiment is several solution compositions that have common physical and biological properties, particularly high stability and low toxicity.

The following examples provide the steps that led to the formulation of the new carrier solution and subsequent testing of those solutions.

EXAMPLES

In Example 1 a new carrier solution is disclosed. Example 2 shows the acceptability of the carrier for whole kidneys without cryoprotectants and Example 3 shows the acceptability of the carrier for whole kidneys containing cryoprotectants. Example 4 presents experiments using the solution for the treatment of rabbit kidneys. Example 5 presents the results of additional experiments combining observations made on kidney slices and on the physical stability of the solutions and comparing these results to previously disclosed results and high recovery of function in kidney slices vitrified in the new solutions containing LM5.

Example 1

Some of the design steps that led to the formulation of the new carrier solution, called LM5, are as follows.

First, there was a need to reduce the concentration of glucose to an unknown extent in order to prevent inactivation of the X1000 antinucleator product described above. Second, the glucose had to be replaced with some other impermeant species. The impermeants of the widely-known and widely-disclosed University of Wisconsin solution (UW Solution, sold under the trademark of VIASPAN) were considered both biologically damaging and prohibitively expensive. Further, impermeants had to be selected that did not share the X1000-inactivating effect of glucose, a formerly unexplored issue. In addition, mannitol, a nominally inert impermeant, was reported by Khirabadi et al. to produce paradoxical vascular damage to the kidney when used in place of glucose in a carrier solution for a VS4-type vitrification solution (Arnaud, Fahy, and Khirabadi, *Cryobiology* 35:358, 1997). Other impermeants known in the art tend to be charged, but charged species might be detrimental due to their ability to chelate ions, among other reasons (see Fahy, da Mouta, et al., 1995, cited above). Sucrose, a popular impermeant, was considered undesirable due to its high viscosity and reported nephrotoxicity. In addition, it was desired to use impermeants that were inexpensive and biologically benign.

Another design consideration stemed from the fact that carrier solutions used in vitrification solutions are best prepared as concentrates. Typically, for example, a 5-fold concentrated version of a carrier solution will be prepared. The vitrification solution is made by, for example, adding one-fifth volume of the concentrate to a graduated or volumetric container, following this with addition of the cryoprotective agents and any necessary polymers, and finally bringing the volume of the entire system to one volume (five times the concentrate volume) so as to dilute the concentrate in water plus cryoprotectants to attain the proper concentration of the carrier solution constituents per unit volume. In order for this to be possible, the constituents of the carrier solution have to be soluble when concentrated approximately five-fold in the presence of the other constituents.

Surprisingly, there is no prior example of the use of lactose in an organ preservation solution or perfusate. The natural existence of lactose in living systems encouraged its use in place of glucose in RPS-2, but it was found to have inadequate solubility to be used in concentrates, and its solubility in the presence of full-strength vitrification solutions was questionable.

As previously noted, the use of mannitol as a perfusate constituent was contradicted by Khirabadi et al.

(*Cryobiology* 35:357, 1997), who found it to be damaging. The use of mannitol is also questionable because of its typical use as an osmotic buffer in organ cryoprotectant perfusions (see Kheirabadi and Fahy, 2000, and Fahy and Ali, 1997, for example). The more mannitol that is present extracellularly, the more is the likelihood that some will leak into the cell, where it will become trapped, creating subsequent damaging cellular swelling. In addition, mannitol is not very soluble in water, and it is less soluble in the presence of cryoprotective agents, limiting its possible concentration as an osmotic buffer.

In addition to these limitations, there is the issue, for both mannitol and lactose, of the solubility of the agent at deep subzero temperatures during cooling to and warming from the glass transition temperature. Typically, many molecules of marginal solubility may precipitate from solution in the cold.

These difficulties were resolved as follows. First, it was determined that retaining 90 mM of the normal 180 mM glucose in RPS-2 was acceptable with respect to compatibility with X1000's antinucleating ability. Next, it was determined that the solubility of mannitol and the solubility of lactose could be accommodated by using each in equal concentrations of 45 mM, replacing a total of 90 mM glucose in RPS-2. The resulting solution was named LM5. The name refers to the use of lactose and mannitol to replace 50% of the glucose in RPS-2. Another solution, LT5, is also efficacious, but is far more expensive than LM5. LT5 consists of RPS-2 in which 45 mM glucose has been replaced by lactose and 45 mM glucose has been replaced by trehalose. As will be shown, at the concentrations in LM5, both mannitol and lactose remain in solution in the presence of cryoprotectants and during cooling and warming to deep subzero temperatures.

TABLE 2

High-Stability, Low-Toxicity Cryoprotectant Solutions Containing LM5

| No. | Wrcrit | Penetrating Cryoprotect. | Polymer(s) | Carrier | % w/v | K/Na (40) | SEM | K/Na (20) | SEM | K/Na (30) | SEM | % K/Na: after −110° C. |
|---|---|---|---|---|---|---|---|---|---|---|---|---|
| 1 | 2.9 | Veg-3% D(1)F + 7% EG | 1% X1000 + 4% dG | LM5 | 64 | 80.5* | 2.5* | | | 95.3 | 1.25 | |
| 2 | 5 | Veg-3% D(1)F + 7% Acetol | 1% X1000 + 4% dG | LM5 | 64 | 80.7 | 1.88 | | | 94.7 | 2.38 | 95 |
| 3 | 10 | Veg-3% D(1)F | 1% X1000 + 1% dG + 7% PVP 5,000 | LM5 | 61 | 84.2 | 1.7 | 96.3 | 2.2 | 100 | 2.06 | |
| 4 | 11.7 | 55% E[D(.7)F]*** | 0.5% X1000 + 0.5% dG + 6% PVP 5,000 | LM5 | 62 | 78 | 1.57 | 90.8 | 3.12 | | | |
| 5 | 14.1 | Veg-4% D(1)F | 0.5% X1000 + 0.5% dG + 7% PVP 5,000 | LM5 | 59 | 89.2 | 1.37 | 96.3 | 2.58 | | | |
| 6 | 19.4 | Veg-3% D(1)F | 7% PVP 5,000 | LM5 | 59 | 95.5 | 1.42 | (est) | | | | |
| 7 | 22.2 | 52% w/v Veg | 0.5% X1000 + 0.5% dG + 6% PVP 5,000 | LM5 | 69 | 89.3 | 1.61 | 94.7 | 2.22 | | | |
| 8 | 42.7 | Veg | 4.25% PVP 5,000 | LM5 | 59.25 | 85.5 | 0.6 | (est) | | | | |
| 9 | 60.3 | Veg | 1% X1000 | LM5 | 56 | 88.7 | 2.22 | (est) | | | | |

All %s are in w/v units;
dG = decaglycerol;
K/Na (40) = K/Na after exposure at 0° C. for 40 min;
K/Na (20) = K/Na after exposure at 0° C. for 20 min;
K/Na (30) = K/Na after exposure at −22° C. for 30–40 min;
SEM = standard error of the mean, usually for 12 samples;
Wrcrit = the warming rate that limits ice formation during warming to no more than 0.2% of sample mass, based on the average of duplicate or triplicate samples (degrees C./min).
X1000 is a commercially-available product from 21st Century Medicine and consists of 80% hydrolyzed polyvinyl alcohol with a relative average molecular mass of around 2 kilodaltons or less.
PVP 5,000 is polyvinylpyrrolidone with an average relative molecular mass of 5 kilodaltons.
VEG is 16.84% w/v ethylene glycol plus 13.96% w/v formamide plus 24.2% DMSO (total concentration 55.00% w/v), Dn(Y) = DMSO in an n:1 mole ratio of D to Y, where Y is another cryoprotectant.
LM5 contains 90 mM glucose, 45 mM lactose, 45 mM mannitol, 7.2 mM $K_2HPO_4$, 1 mM $CaCl_2$, 2 mM $MgCl_2$, 5 mM reduced glutathione, 28.2 mM KCl, 10 mM $NaHCO_3$, and 1 mM Adenine HCl.
Many other formulas based on the above have been tested and found to yield 100% recovery of K/Na ratio after exposure at −20° C. for 20 min, but the critical warming rates for these solutions have not been determined.

TABLE 3

Some High-Stability, Low-Toxicity Cryoprotectant Compositions Containing LM5

| No. | Wrcrit | Penetrating Cryoprotect. | Polymer(s) | DMSO | Form. | EG | Acetol |
|---|---|---|---|---|---|---|---|
| 1 | 2.9 | Veg-3% D(1)F + 7% EG | 1% X1000 + 4% dG | 22.305 | 12.858 | 23.837 | 0 |
| 2 | 5 | Veg-3% D(1)F + 7% Acetol | 1% X1000 + 4% dG | 22.305 | 12.858 | 16.837 | 7 |
| 3 | 10 | Veg-3% D(1)F 7% PVP 5,000 | 1% X1000 + 1% dG + | 22.305 | 12.858 | 16.837 | 0 |
| 4 | 11.7 | 55% E[D(.7)F]$_{38\ 15}$ 6% PVP 5,000 | 0.5% X1000 + 0.5% dG + | 20.926 | 17.234 | 16.84 | 0 |
| 5 | 14.1 | Veg-4% D(1)F 7% PVP 5,000 | 0.5% X1000 + 0.5% dG + | 21.671 | 12.492 | 16.837 | 0 |
| 6 | 19.4 | Veg-3% D(1)F | 7% PVP 5,000 | 22.305 | 12.858 | 16.837 | 0 |
| 7 | 22.2 | 52% w/v Veg 6% PVP 5,000 | 0.5% X1000 + 0.5% dG + | 22.887 | 13.194 | 15.919 | 0 |

TABLE 3-continued

Some High-Stability, Low-Toxicity Cryoprotectant Compositions Containing LM5

| No. | Wrcrit | Penetrating Cryoprotect. | Polymer(s) | DMSO | Form. | EG | Acetol |
|---|---|---|---|---|---|---|---|
| 8 | 42.7 | Veg | 4.25% PVP 5,000 | 24.208 | 13.955 | 16.837 | 0 |
| 9 | 60.3 | Veg | 1% X1000 | 24.208 | 13.955 | 16.837 | 0 |

DMSO: dimethyl sulfoxide;
Form. = formamide;
EG = ethylene glycol;
Acetol = $CH_3COCH_2OH$;
All %s = % w/v; DMSO, form, EG, and Acetol columns refer to % w/v concentrations.
LM5 constituents not shown in this table.
dG = decaglycerol;
PVP 5000 is polyvinylpyrrolidone with an average relative molecular mass of 5 kilodaltons;
X1000 is a commercially-available product from 21st Century Medicine and consists of 80% hydrolyzed polyvinyl alcohol with a relative average molecular mass of around 2 kilodaltons or less;
VEG is 16.84% w/v ethylene glycol plus 13.96% w/v formamide plus 24.2% w/v DMSO (total concentration 55.00% w/v); D(n)Y = DMSO in an n:1 mole ratio of D to Y, where Y is another cryoprotectant;
LM5 contains 90 mM glucose, 45 mM lactose, 45 mM mannitol, 7.2 mM $K_2HPO_4$, 1 mM $CaCl_2$, 2 mM $MgCl_2$, 5 mM reduced glutathione, 28.3 mM KCl, 10 mM $NaHCO_3$, and 1 mM Adenine HCl.

Example 2

Several rabbit kidneys were perfused, at 3.5° C., with LM5 for 5 hours. In addition, during this perfusion, 1% w/v X1000, 1% w/v decaglycerol, and 7% w/v polyvinylpyrrolidone of mean molecular mass 5000 (PVP 5000) were introduced and removed in such a way as to simulate the concentrations of these substances in a typical perfusion with a vitrification solution. The results are shown in FIG. 1, which plots postoperative serum creatinine levels against the postoperative day on which the sample was taken. As can be seen, these kidneys sustained no measurable damage as a result of perfusion with LM5 with and without the cryoprotective polymers. Therefore, LM5 is compatible with both the vascular and the parenchymal components of whole organs.

Example 3

Next, several rabbit kidneys were perfused in an LM5 carrier solution with concentrations of cryoprotectants that are sufficient to vitrify at ambient pressures. Calcium and magnesium were gradually removed and added back as cryoprotectant concentrations were increased and then reduced, in order to avoid precipitation of these ions. There were no perfusion problems attributable to any effect of LM5, and survival and life support on the part of these perfused kidneys was obtained upon transplantation despite the lack of use of iloprost. Organ pretreatment with iloprost in vivo is traditionally mandatory for obtaining survival when rabbit kidneys are perfused with concentrations of cryoprotectant that can vitrify at ambient pressure. These results (not shown) demonstrated that LM5 is compatible with the delivery of vitrifiable concentrations of a highly advanced cryoprotectant formula by vascular perfusion.

Example 4

Figure 2:
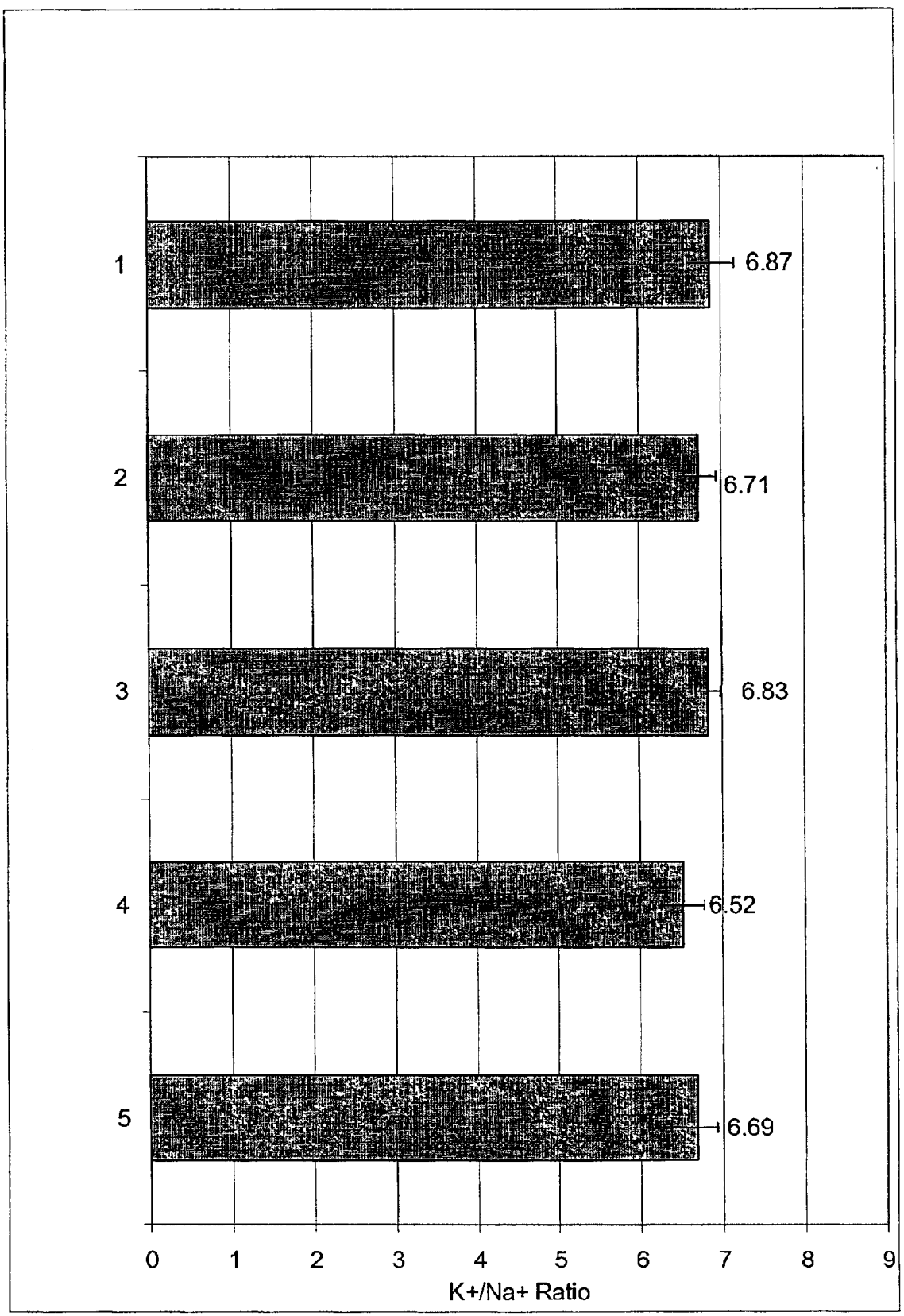
FIG. 2 shows recovery of rabbit renal cortical slices after exposure to vitrification solution variations at about –22° C. in the presence of a carrier solution containing lactose and mannitol.

Next, kidney slices were exposed to a wide variety of cryoprotectant solutions in LM5. LM5 proved to be suitable for use in the presence of vitrifiable concentrations of cryoprotectant. One particular example is shown in FIG. 2, wherein approximately 100% recovery of slice K/Na ratio was obtained in 5 vitrification solution variations after treatment at 0° C. for 20 min. The details of these solutions and the results are given in Table 1.

TABLE 1

Compositions of Solutions

| Bar No. | % of Control K/Na Ratio | Composition of the Vitrification Solution (All in LM5) |
|---|---|---|
| 1 | 100.0 | LM5 only, no cryoprotectant |
| 2 | 97.7 | 16.84% EG + 13.16% F + 22% D + 7% PVP 5000 + 1% X-1000 + 1% decaglycerol |
| 3 | 99.4 | same, but use 0.1% X-1000 + 1.9% decaglycerol |
| 4 | 94.9 | same, but use 1% X-1000 + 2% decaglycerol |
| 5 | 97.4 | same, but use 0.1% X-1000 + 2.9% decaglycerol |

EG = ethylene glycol; F = formamide; D = dimethyl sulfoxide; all percents given in the table are in % w/v. This was experiment 00-035.

The motivation for producing LM5 was to ensure that ice blockers could be used with full effectiveness to maintain the stability of vitrification solutions against ice formation. To investigate the success of LM5 as a carrier for highly stable solutions relying extensively on both X1000 and polyglycerol as ice blockers, the stability of several solutions was measured using a differential scanning calorimeter as described above and below, and the same solutions were tested for their effect on slice viability under a variety of test conditions. These data were then assembled into the viability-stability curve shown in FIG. 3.

Figure 3:
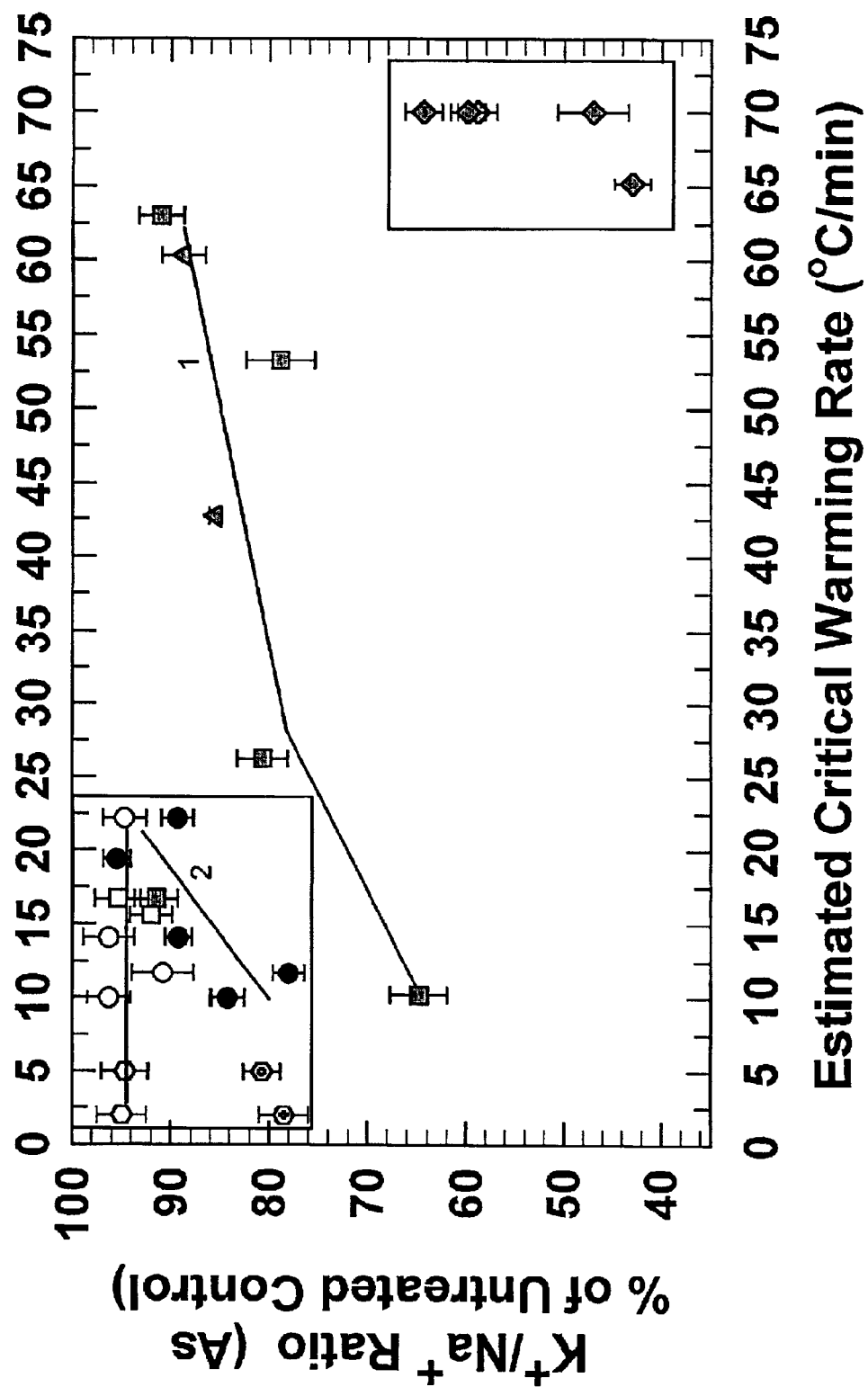
FIG. 3 shows a viability-stability diagram for 16 exemplary vitrification solutions, including both previously described solutions and new variants of extraordinary efficacy, most of which are contained in a carrier solution comprising lactose and mannitol.

FIG. 3 reports viability data represented by the K/Na ratio of rabbit renal cortical slices after exposure to and subsequent washout of the 16 vitrification solutions followed by incubation in Cross-Taggart solution with continuous oxygenation for 90 minutes. K/Na ratio was measured as reported in the scientific literature.

Circle and hexagons in FIG. 3 represent solutions whose exact compositions have not been previously disclosed. Triangles represent solutions that are the virtual equivalent of previously disclosed solutions but that contain an LM5 carrier solution. Squares and diamonds represent solutions previously disclosed in "Improved Cryoprotectant Solutions", U.S. application Ser. No. 09/400,793, filed Sep. 21, 1999 (herein incorporated by reference). All previously-undisclosed compositions contain an LM5 carrier solution.

Empty circles represent the K/Na ratio after a total exposure period of 20 minutes at 0° C. Grey and black circles and other points represent K/Na ratios after 40 minutes of exposure at this temperature. In the case of the hexagons, hexagons with a central mark show K/Na ratios after 30 min of exposure at 0° C., and hexagons with no mark in the center show K/Na ratios after 30 min of exposure at around −22° C.

The horizontal axis, labeled "estimated critical warming rate," represents the warming rate required to prevent more than 0.2% of the mass of the solution from crystallizing during warming. This extent of crystallization is thought to be acceptable in most biological systems. Choosing the warming rate that brings the extent of ice formation to this level provides a standard for comparing the stabilities of all solutions. The lower the warming rate in FIG. 3, the more stable is the solution against ice formation during rewarming (devitrification). The critical warming rate was determined by cooling small (~10–70 mg) samples to below −130° C. at 100° C./min and then warming them in triplicate at several fixed warming rates. The heat evolved during devitrification was recorded using a differential scanning calorimeter and averaged over each set of three determinations, and these averages were plotted against the warming rate. The data were fitted using spline fitting routines, and the warming rate required to produce a canonical evolved heat of 0.67 joules per gram of solution according to the spline fit was chosen as the critical warming rate. (One gram of water, upon freezing, releases, 80 calories, or 335 joules, of heat. Therefore, the critical heat evolution was set as 335 joules× 0.002=0.67 joules.)

The desirable features of vitrification solutions are high stability and lack of toxicity. The standard solution, VS41A, was studied in either Euro-Collins (leftmost diamond) or RPS-2 (remaining diamonds) carriers, with the results shown within the box at the lower right hand corner of FIG. 3. VS41A, exposed using the older carrier solutions, has relatively low stability (high critical warming rate) and high toxicity (relatively low K/Na ratio).

Looking at the gray squares on the diagram, and rough equivalents prepared in LM5 (gray triangles), the trend noted in U.S. patent application Ser. No. 09/400,793, filed Sep. 21, 1999, is confirmed, in which there is a tendency for K/Na to be lower as the critical warming rate becomes lower. It can be seen that the two solutions containing LM5 perform perfectly satisfactorily in terms of their support of viability at their respective stabilities, although no direct comparisons were made on these precise solutions prepared in other carriers.

Previously-undescribed solutions of extreme stability and non-toxicity are enclosed in the box at the upper left hand corner of the figure. Seven out of nine such solutions were prepared in LM5 and all were tested for periods of 20 to 40 minutes of exposure. The black circles in the box show a trend (trend line 2) similar to that shown for the previously-disclosed solutions (trend line 1) in that greater stability is associated with a trend toward lower K/Na ratio, but trend line 2 is clearly above and to the left of the previously-discussed trend line 1, a highly desirable improvement.

No such trend is applicable to the case of 20-minute exposure at 0° C. or to 30-min exposure at −22° C. (empty points): recovery of 95% of the activity of untreated control slices may be obtained even for vitrification solutions that are stable when rewarmed at rates as low as 2.9° C./min, an astonishing improvement.

Table 2 lists the composition, biological effect, and stability of each of the subject solutions containing LM5. RPS-2 contains 180 mM glucose as a major component as well as 7.2 mM $K_2HPO_4$, 1 mM $CaCl_2$, 2 mM $MgCl_2$, 5 mM reduced glutathione, 28.2 mM KCl, 10 mM $NaHCO_3$, and 1 mM Adenine HCl. LM5 contains 90 mM glucose, 45 mM lactose, 45 mM mannitol, 7.2 mM $K_2HPO_4$, 1 mM $CaCl_2$, 2 mM $MgCl_2$, 5 mM reduced glutathione, 28.2 mM KCl, 10 mM $NaHCO_3$, and 1 mM Adenine HCl (The 180 mM glucose in RPS-2 is replaced with 90 mM glucose plus 45 mM lactose plus 45 mM mannitol in LM5). Table 2 also lists some results after cooling slices to −110° C. or below in some of the most advantageous solutions, showing unprecedented success after vitrification of kidney tissue. The formulas that gave the best results after vitrification had nonpenetrating solution component (LM5 plus polymers) tonicities totaling 1.5 times isotonic. A useful tonicity range for vitrification solutions is 1.1 to 2.0 times isotonic or, more favorably, 1.2 to 2.0 times isotonic or, more favorably, 1.2 to 1.5 times isotonic. Although not included in Table 2, the solutions represented by the Grey and white squares in FIG. 1 in the upper left corner box are expected to be even more stable and no more toxic when composed with an LM5 carrier solution, since these solutions contained an RPS-2 carrier, which limits the effectiveness of the antinucleator in the solution. Table 3 provides the explicit compositions of the solutions of Table 1.

To analyze LM5 as a flush and store solution for rabbit kidneys, about 8 rabbit kidneys were flushed with LM5 and stored on ice for 5 hours and then transplanted. Except for two cases in which creatinine suddenly peaked and then suddenly declined for reasons not clearly related to problems with the preservation, all kidneys performed well after transplantation, suggesting that LM5 is compatible not only with perfusion but also with cold storage without perfusion, as prior to and after cryopreservation.

In summary, solutions are reported that minimize toxicity, cooling injury, and devitrification. These solutions, used at full strength, are of particular importance for the cryopreservation of larger living systems, such as organs and engineered tissues and bioartificial organs, for which rapid cooling and warming is difficult or impossible. However, many living systems and some engineered tissues and bioartificial organs are capable of being cooled and warmed at higher rates than those discussed herein, or are capable of survival after more severe ice formation than is discussed herein. For these systems, appropriate dilutions of the tabulated formulas may also be effectively used, and may be more advantageous than the full strength versions. The use of dilutions of established vitrification solutions is taught, for example, in Rall, W. F., and Fahy, G. M., *Nature*, 313:573–575, 1985. Consequently, moderate dilutions of the presently disclosed formulae are considered to be equivalent to and to fall within the scope of the embodiments described herein.

What is claimed is:

1. In a solution for the introduction and washout of vitrifiable concentrations of cryoprotectants in a viable cell, tissue or organ, the improvement comprising inclusion of mannitol, lactose and vitrifiable concentrations of cryoprotectant in the solution, wherein said cryoprotectant comprises dimethyl sulfoxide, formamide, and ethylene glycol.

2. In a solution for the introduction and washout of vitrifiable concentrations of cryoprotectants in a viable cell, tissue or organ, the improvement comprising inclusion of mannitol, lactose and vitrifiable concentrations of cryoprotectant in the solution, wherein said cryoprotectant comprises polyvinyl alcohol, or a copolymer of vinyl alcohol and vinyl acetate.

3. In a solution for the introduction and washout of vitrifiable concentrations of cryoprotectants in a viable cell, tissue or organ, the improvement comprising inclusion of mannitol, lactose and vitrifiable concentrations of cryoprotectant in the solution, wherein said cryoprotectant comprises one or more of polyglycerol and polyvinylpyrrolidone.

4. In a carrier solution for the introduction and washout of vitrifiable concentrations of cryoprotectants in a viable cell, tissue or organ, the improvement comprising inclusion of mannitol, lactose and 90 mM glucose in the solution.

5. A carrier solution for the introduction and washout of vitrifiable concentrations of cryoprotectants in a viable cells, tissue or organ, said solution comprising: 45 mM of mannitol, 45 mM lactose, 7.2 mM potassium phosphate, 5 mM reduced glutathione, 28.2 mM potassium chloride, 10 mM sodium bicarbonate, and 1 mM adenine HCl.

6. The solution of claim 5 further comprising 1 mM $CaCl_2$ and 2 mM $MgCl_2$.

7. In a solution for the introduction and washout of vitrifiable concentrations of cryoprotectants in a viable cell, tissue or organ, the improvement comprising inclusion of mannitol, lactose and vitrifiable concentrations of cryoprotectant in the solution, wherein said solution further comprises polymers selected from the group consisting of: polyglycerol, polyvinylpyrrolidone, polyvinyl alcohol, and a copolymer of vinyl alcohol and vinyl acetate, and wherein said solution has a tonicity of between 1.1 to 2.0 times that of a solution that does not cause osmotic volume changes of said cell, tissue or organ.

8. In a carrier solution for the introduction and washout of vitrifiable concentrations of cryoprotectants in a viable cell, tissue or organ, the improvement comprising inclusion of mannitol and lactose in the solution, wherein said solution has a tonicity of between 1.1 to 2.0 times that of a solution that does not cause osmotic volume changes of said cell, tissue or organ.

9. In a carrier solution for the introduction and washout of vitrifiable concentrations of cryoprotectants in a viable cell, tissue or organ, the improvement comprising inclusion of mannitol and lactose in the solution, wherein the lactose and mannitol are each present at 45 mM.

10. In a carrier solution for the introduction and washout of vitrifiable concentrations of cryoprotectants in a viable cell, tissue or organ, the improvement comprising inclusion of mannitol and lactose in the solution, further comprising 10mM bicarbonate.

11. In a solution for the introduction and washout of vitrifiable concentrations of cryoprotectants in a viable cell, tissue or organ, the improvement comprising inclusion of mannitol, lactose and vitrifiable concentrations of cryoprotectant in the solution, wherein said solution further comprises polymers selected from the group consisting of: polyglycerol, polyvinylpyrrolidone, polyvinyl alcohol, and a copolymer of vinyl alcohol and vinyl acetate, said solution having a tonicity of 1.2 to 2.0 times that of a solution that does not cause osmotic volume changes of said cell, tissue or organ.

12. In a solution for the introduction and washout of vitrifiable concentrations of cryoprotectants in a viable cell, tissue or organ, the improvement comprising inclusion of mannitol, lactose and vitrifiable concentrations of cryoprotectant in the solution, wherein said solution further comprises polyvinylpyrrolidone.

* * * * *